United States Patent
Pauly

(10) Patent No.: US 6,465,023 B2
(45) Date of Patent: *Oct. 15, 2002

(54) **COSMETIC, DERMATOLOGICAL AND PHARMACEUTICAL USE OF AN EXTRACT OF *TERMINALIA CATAPPA***

(75) Inventor: Gilles Pauly, Nancy (FR)

(73) Assignee: Laboratoires Serobiologiques (Societe Anonyme), Pulnoy (FR)

(*) Notice: Subject to any disclaimer, the term of this patent is extended or adjusted under 35 U.S.C. 154(b) by 4 days.

This patent is subject to a terminal disclaimer.

(21) Appl. No.: 09/767,146

(22) Filed: Jan. 23, 2001

(65) Prior Publication Data

US 2001/0002265 A1 May 31, 2001

Related U.S. Application Data

(60) Division of application No. 09/268,700, filed on Mar. 16, 1999, now Pat. No. 6,217,876, and a continuation of application No. PCT/FR97/01468, filed on Aug. 7, 1997.

(30) Foreign Application Priority Data

Sep. 16, 1996 (FR) .............................. 96 11403

(51) Int. Cl.⁷ ..................... A01N 65/00; A61K 35/78; A61K 7/48
(52) U.S. Cl. ....................... 424/769; 424/725
(58) Field of Search .................. 424/725, 769

(56) References Cited

U.S. PATENT DOCUMENTS 6,217,876 B1 * 4/2001 Pauly .................... 424/725

FOREIGN PATENT DOCUMENTS

WO    98/27956    7/1998

OTHER PUBLICATIONS

Ghazanfar "Handbook of Arabian Medicinal Plants" Combretaceae *Terminalia catappa* L., CRC Press, 1994, p. 87.
R. Gupta et al., Chemical Abstract, vol. 99, 1983.
M. Esposito–Avella et al., Chemical Abstract, vol. 103, 1985.
M. Joyeux et al., Chemical Abstract, 1995.

* cited by examiner

Primary Examiner—Herbert J. Lilling
(74) Attorney, Agent, or Firm—Young & Thompson

(57) ABSTRACT

The invention concerns the use of an extract of the *Terminalia catappa* plant, as well as cosmetic, dermatological and pharmaceutical compositions containing such an extract. The invention also concerns the use of an extract of the *Terminalia catappa* plant with other active compounds, in a cosmetic, dermatological and/or pharmaceutical composition for external topical use for the skin or superficial body growth.

3 Claims, No Drawings

COSMETIC, DERMATOLOGICAL AND PHARMACEUTICAL USE OF AN EXTRACT OF *TERMINALIA CATAPPA*

CROSS-REFERENCE TO RELATED APPLICATIONS

This application is a division of application Ser. No. 09/268,700, filed Mar. 16, 1999 now U.S. Pat. No. 6,217,876.

This application is a continuation of international application PCT/FR97/01468 filed on Aug. 7, 1997, which designates the United States of America, and corresponds to French application 96.11403 of Sep. 16, 1996, the disclosure of which is incorporated herein by reference.

The present invention relates to the fields of cosmetology and dermatology and has for its object the use for cosmetic, dermatological or pharmaceutical uses, of an extract of the plant *Terminalia catappa*, as well as a corresponding cosmetic, dermatological or pharmaceutical composition.

The plant *Terminalia catappa* or "Indian terminalia" is a very common species, of Indian origin and of the family Combretun.

It is a tree 5 to 25 meters high, whose branches are horizontal and sub-verticulated, particularly at the top of the young plants.

The leaves are alternate, whole, membranous and distinct as a function of age.

Defoliation takes place at the end of the dry season, the leaves turning red before falling.

The wide geographic distribution, tropical and subtropical, of the *Terminalia catappa* plant partially explains its widespread use in popular African, Asiatic and American medicines, for many years.

Externally used, the *Terminalia catappa* plant is above all used for the care of dermatological and rheumatoid afflictions.

Internally, this plant is used for the treatment of gastrointestinal, respiratory and cardiovascular afflictions.

All portions of the plant (leaves, bark, roots, fruit, wood) are used in traditional medicine.

The extract of the bark of the stems is used externally for its astringent action (tannins) in the case of wounds and ulcerations.

Nevertheless, it is above all the leaves, alone or in association with other plants, which are used for the treatment of dermatological and rheumatoid afflictions.

The juice obtained after pressing the leaves is used in the treatment of scabies, leprosy, prurigo and scabbing (Senegal) and in the treatment of wounds (Madagascar, New Guinea).

In India, the plant has been used in the Ayurvedic and Unani medical systems: the juice of the young leaves is used in the treatment of scabies and other cutaneous disorders. A hemostatic effect is sometimes mentioned.

The leaves can be applied to aching joints giving rise to an analgesic effect (Caribbean, Senegal, Indochina, Malaysia).

In the form of local compresses, the crushed green leaves coated with castor oil are used to relieve lumbago.

Associated with other plants, and in an oily vehicle, it is used for the care of sprains and/or muscular pain (Cook Islands).

Internally, the leaves of *Terminalia catappa* are used for the treatment of gastric disorders (Senegal), respiratory afflictions (Caribbean, Haiti, Mexico, Cuba, New Guinea), cardiovascular afflictions (anti-hypertensive action) and hypatic afflictions (Creole medicine), insomnia (Creole medicine) and gonorrhoea (Madagascar), or as an anti-diarrhetic (Indochina, India).

It has on the other hand been shown, on isolated hypatic cells, that the extracts of the leaves, in vitro, have anti-lipidoperoxidant and anti-hypatotoxic properties.

The anti-radical activity of extracts has also been demonstrated in vitro by the test for the decoloration of diphenyl-picryl-hydrazyl radical (DPPH) (Joyeux M. et al. PHYTOTHERAPY RESEARCH, 1995, 9.228–230).

Moreover, there is also known from various texts the use in cosmetic extracts of species of *Terminalia chebula* and *Terminalia bellerica* for the treatment of cutaneous disorders, as anti-hyaluronidase active ingredients or active ingredients inhibiting 5α-reductase or as having anti-oxidant activity (see particularly GB-2 274 058, JP-0 6009371, JP-0 5255102 and JP-0 4069343).

Finally, it is also known to use as anti-inflammatories, the complexes formed by vegetable saponines extracted from *Terminalia sericea* combined with phospholipids (see particularly U.S. Pat. No. 5,166,139).

However, the use of extracts of *Terminalia catappa*, for external topical application, in the field of cosmetology and/or pharmacy has not been known.

Accordingly, the inventor of the present invention has determined, in an unexpected and surprising manner, that the extracts of *Terminalia catappa* have specific biological activities, which render them directly usable in cosmetic, dermatological and pharmaceutical preparations or compositions for external topical use.

Thus, the principal object of the present invention consists in the use of an extract of the plant *Terminalia catappa*, alone or in association with other active compounds, in a cosmetological, dermatological and/or pharmaceutical composition for external topical use for the skin and the nails.

The inventor has particularly noted that the extract of the plant *Terminalia catappa* has pronounced anti-inflammatory, soothing, astringent, firming, protective and anti-stress repairing properties (UV-R, pollution, various mechanical, physical and chemical damage) in the scope of the mentioned use.

According to a preferred embodiment of the invention, the extract of the plant *Terminalia catappa* is obtained from the leaves of this plant.

According to a particularly preferred characteristic, the solvent used for the preparation of the extract of the plant *Terminalia catappa* is selected from the group consisting of water, aqueous solutions (of different pH), alcohols (methanol, ethynol, propynol, isopropynol . . . ) ketones (acetone, methylketone, diethylketone . . . ), halogenated hydrocarbons, esters (ethyl, propyl or butyl acetate), polyols (glycols, diethylene-glycol, propanediol, dipropylene glycol, butylene glycol . . . ) and mixtures of two or more of the mentioned solvents.

Obtaining the preparation of the mentioned extract can be carried out by different known methods at least in part by of one skilled in the art.

By way of non-limiting example, there will be described hereafter different processes for possible obtention of an extract of *Terminalia catappa* used in the field of the present invention.

Example I 100 grams of leaves of *Terminalia catappa* are introduced into Erlenmeyer flasks, after having been roughly crushed.

There is then poured a liter of distilled water, at the boiling point with reflux, on the said leaves and this mixture is left to infuse/macerate in an autoclave at 37° C. for 24 hours.

The macerate is then successively filtered on Whatman type filter paper, concentrated and under vacuum by means of a rotating evaporator, and finally concentrated in a current of nitrogen to the formation of a dry extract.

The yield of this extraction is 12.6% by weight relative to the initial leaves.

Example II 100 grams of leaves of *Terminalia catappa* are processed as in Example I, the extraction solvent being 90° alcohol, and not water (as in Example I).

The yield of this extraction is 6.4% by weight relative to the initial leaves.

Example III

There are introduced two liters of distilled water into a reactor and there is then added 200 grams of leaves of crushed *Terminalia catappa*.

Extraction is then carried out with agitation for one hour at about 80 to 90° C., the resulting liquid being, after cooling to ambient temperature, centrifuged or filtered to separate the extract.

There is thus obtained 1.57 liters of a dark brown extract containing 3.50% by weight of dry extract.

The moist residue is extracted under the same conditions by means of two liters of water and there is thus recovered 1.73 liters of a brown extract, containing 0.80% by weight of dry extract.

The two above extracts are atomized and there are recovered 33.46 grams of powder for the first extract and 11.6 grams of powder for the second extract, which corresponds to a total yield of the extraction of 22.5% by weight relative to the leaves.

Example IV

There is introduced one liter of absolute ethanol into a reactor and 200 grams of crushed *Terminalia catappa* leaves are added.

There is then carried out an extraction with reflux and agitation for one hour, the resultant liquid being, after cooling to room temperature, filtered to separate the extract of dark green color.

An extraction is then carried out under the same conditions, of the residue, by means of one liter of ethanol, this latter being then evaporated under vacuum at 35–40° C. and the obtained residue being dried in an autoclave at 40–50° C.

This process permits obtaining 36.84 grams of paste from the first extract and 15.2 grams from the second extract, which corresponds to a total extraction yield of 26% by weight relative to the leaves.

The extracts of *Terminalia catappa* obtained by means of the processes described above, contain particularly flavonoids, polyphenols, saponosides, triterpenes, diterpenes, catechuic tannins and tannoid derivatives.

To determine in particular the anti-inflammatory activity of the extracts of the plant *Terminalia catappa*, the inventor has conducted various experiments under conditions of use and the obtained results are described hereafter.

To carry out these experiments, there were used Sprague-Dawley (Iffa Credo) rats weighing about 150 to 250 grams. These animals were stabilized for 15 days preceding the test, in macrolon cages, the animal environment being cycled and thermostated (12 hours by day, 12 hours by night; 20 to 22° C.).

Before any treatment, the volume of the right rear paw of each rat was measured (vo) with the aid of a plethysmometer (Ugo Basile 7150, Apelex).

The products to be tested were administered intraperitoneally at a dose corresponding to 400 mg of dry plant/kg, and a volume of 1 ml/kg and the test lots received physiological serum intraperitoneally.

Each rat then received an injection, in the pad of the right rear paw, of 0.05 ml of carrageenin diluted to 1% in deionized water.

Then the volume of the paw was measured (vt) at the peak of inflammation, namely three hours after injection with the inflammatory agent.

A Randall-Selito test was performed when the extract was deemed to be sufficiently active. This test was carried out with the aid of a pressure analgesimeter, permitting determining the pain threshold by exerting a force with a teflon cone on the right rear paw.

The extracts injected intraperitoneally corresponded to aqueous and ethanol extracts prepared according to Examples I and II above, and the tested doses equaled, in terms of raw extract, 50.4 mg of raw extract/kg for the aqueous extract and 25.6 mg of raw extract/kg for the ethanol extract.

The mean percentages of inhibition of edema were calculated for the different surveys from differences obtained between the mean measured volumes before (vo) and after (vt) injection of the carrageenin, according to the following formula:

$$\frac{[(vt-vo) \text{ sample} - (vt-vo) \text{ treated } 1 \times 100}{(vt-vo) \text{ sample}}$$

For the Randall-Selitto test, the pain threshold observed (retraction of the paw or outcry) was expressed in grams.

The statistical comparisons were carried out with the help of the ANOVA test, according to a test t not paired for the edema test with carrageenin, and for the non-parametric Mann-Whitney test, followed by a non-paired test with the Randall-Selitto test.

The experiments described below gave the results set forth in the following tables:

| Test of edema with carrageenin | | | |
|---|---|---|---|
| Test rats | | | |
| No. rats | Vo | V 3h | Δ V |
| 1 | 1.85 | 3.30 | 1.45 |
| 2 | 1.90 | 3.27 | 1.37 |
| 3 | 1.87 | 3.25 | 1.38 |
| 4 | 1.87 | 3.27 | 1.40 |
| Average | 1.87 | 3.27 | 1.40 |
| SEM | 0.01 | 0.01 | 0.02 |
| Treated rats (ethanol extract) | | | |
| No. rats | Vo | V 3h | ΔV | % inhibition |
| 5 | 1.84 | 2.50 | 0.66 | |
| 6 | 1.91 | 2.58 | 0.67 | |

-continued

Test of edema with carrageenin

| 7 | 1.85 | 2.53 | 0.68 | |
| 8 | 1.87 | 2.54 | 0.67 | |
| Average | 1.87 | 2.54 | 0.67* | 52.11 |
| SEM | 0.02 | 0.02 | 0.00 | |

Treated rats (aqueous extract)

| No. rats | Vo | V 3h | ΔV | % inhibition |
| --- | --- | --- | --- | --- |
| 9 | 1.80 | 2.51 | 0.71 | |
| 10 | 1.90 | 2.55 | 0.65 | |
| 11 | 1.75 | 2.67 | 0.92 | |
| 12 | 1.82 | 2.58 | 0.76 | |
| Average | 1.82 | 2.58 | 0.76** | 45.66 |
| SEM | 0.03 | 0.03 | 0.06 | |

*significant difference relative to the test: p = 0.0001
**significant difference relative to the test: p = 0.0001
ANOVA non-paired test Randall-Selitto Test

| Test rats | | Rats treated with an extract of Terminalia catappa | |
| --- | --- | --- | --- |
| No. rat | Pain threshold (g) | No. rat | Pain threshold (g) |
| 1 | 80 | 5 | 140 |
| 2 | 65 | 6 | 120 |
| 3 | 70 | 7 | 110 |
| 4 | 55 | 8 | 130 |
| Average | 67.50 | Average | 125.00*** |
| SD | 10.41 | SD | 12.91 |
| SEM | 3.29 | SEM | 4.27 |

***significant difference relative to the test: p = 0.0004 (Mann-Whitney test followed by a non-paired test).

It is clearly apparent from the results shown in the above tables that the extracts of *Terminalia catappa* had particularly a marked anti-inflammatory activity.

The present invention also has for its object compositions or cosmetic, dermatological or pharmaceutical topical preparations for the skin, the hair or the nails, and more generally peripheral growths, characterized in that they contain particularly, as active ingredients, cosmetically or pharmaceutically effective quantities of extracts of the plant *Terminalia catappa*, obtained for example according to any one of the above methods.

Although the present description specifies more particularly the extracts obtained from leaves of the plant *Terminalia catappa*, it is of course also possible to obtain extracts having analogous activities and prepared according to similar processes, from other parts of the *Terminalia catappa* plant, such as for example the stems or the roots.

The cosmeto-dynamic activities or, as the case may be, therapeutic activities, of these compositions or preparations comprising extracts consist in particular in pronounced local anti-inflammatory, soothing, firming and astringent activities on the skin, anti-aging of the skin and anti-irritant activities for the skin and scalp.

According to a preferred embodiment of the invention, the cosmetic, dermatologic or pharmaceutical composition comprises between 0.005% and 20% by weight, preferably between 0.10% and 3% by weight, of an extract of the *Terminalia catappa* plant, obtained for example by means of one of the four extraction processes described above.

Said extracts could be used as desired either as they are (liquid, paste, dry), or after preparation in the form of microspheres, microcapsules, nanocapsules, liposomes or other analogous known forms.

The cosmetic, dermatologic or pharmaceutical compositions or preparations recited above could have any galenic form usually used for this type of product, namely particularly gels, hydrogels, creams, pomades, milks, shamos, capillary lotions, soaps, oil/water or water/oil emulsions, multiple emulsions, makeup or the like.

By way of examples of practical embodiments of the invention, there will be described hereafter different cosmetic or dermatologic products or preparations, comprising an extract of the *Terminalia catappa* plant.

Example 1

A cosmetic product in the form of a framing and soothing cutaneous emulsion according to the invention can, for example, have a weight composition as indicated hereafter (association of the fractions A and B):

The process for preparation of the above emulsion consists in separately heating fractions A and B to 80° C., then introducing fraction A into fraction B at 80° C. and with turbine agitation, then cooling the mixture to 50° C. while continuing the turbine agitation, and finally subjecting the mixture to planetary agitation at 50° C. and cooling it to room temperature.

Example 2

A cosmetic product in the form of a capillary emulsion according to the invention can for example have a weight composition as indicated hereafter (association of fractions A, B and C):

| FRACTION A: | |
| --- | --- |
| Glycerol stearate (and) PEG stearate 100 | 2.000 |
| Cetostearyl alcohol (and) dipalmitoylethyl-hydroxyethylammonium methosulfate | 2.500 |
| Cetyl alcohol | 3.000 |
| Dimethicone | 2.000 |
| FRACTION B: | |
| Water | 87.300 |
| Elestab ® 4121 (Serobiologic Laboratories) | 0.400 |
| Hydroxypropyltrimonium chloride/hydroxypropyl guar gum | 0.500 |
| Extract of *Terminalia Catappa* (obtained by the process of Example II) | 2.000 |
| FRACTION C: | |
| Perfume | 0.300 |

The process for preparation of the above capillary emulsion consists in separately heating fractions A and B to 75° C., then introducing fraction A into fraction B at 75° C. with turbine agitation, then cooling the mixture to 60° C. whilst continuing turbine agitation, subjecting the mixture to planetary agitation at 60° C. and cooling it, adding fraction C at 40° C. and finally continuing cooling to ambient temperature.

Example 3

A cosmetic product in the form of a soothing and refreshing emulsion, for application after exposure to the sun, according to the invention, can for example have a weight composition as indicated hereafter (association of the fractions A, B and C):

| FRACTION A: | |
|---|---|
| Glycerol stearate (and) PEG 100 stearate | 1.500 |
| Cetostearyl alcohol (and) Ceteh-20 | 1.500 |
| Cetyl alcohol | 1.000 |
| Caprilic/capric triglyceride | 8.000 |
| Cetostearyl isononanoate | 4.000 |
| Octyldodecanol | 3.000 |
| Dimethicone | 0.500 |
| Elestab ® 4121 (Serobiologic Laboratories) | 0.300 |
| FRACTION B: | |
| Water | 73.550 |
| Elestab ® 4121 (Serobiologic Laboratories) | 0.400 |
| *Terminalia Catappa* extract (obtained by the process of Example III, diluted to 10% in butylene glycol) | 5.000 |
| Xanthane gum | 0.500 |
| FRACTION C: | |
| Polyacrylamide (and) isoparaffin (and) Laureth-7 | 0.750 |

The process for preparation of the above emulsion consists first in turbining fraction B before forming the emulsion, then heating separately the fractions A and B to 80° C., introducing fraction A into fraction B at 80° C. with turbine agitation, cooling the obtained mixture to 60° C. while maintaining turbine agitation, then adding fraction C at 60° C. with turbine agitation and continuing cooling and, finally, cooling to ambient temperature while carrying out planetary agitation from 50° C.

Example 4

A cosmetic product in the form of a soothing and astringent emulsion for the face (sensitive skin) according to the invention can for example have a weight composition as indicated hereafter (association of the fractions A and B):

| FRACTION A: | |
|---|---|
| Sorbitan palmitate | 3.500 |
| Glycerol stearate | 1.500 |
| Cetyl alcohol | 2.500 |
| Cetostearyl isononanoate | 7.000 |
| Octyldodecanol | 5.500 |
| Parafin oil | 3.000 |
| Dimethicone | 2.000 |
| Elestab ® 4121 (Serobiologic Laboratories) | 0.300 |
| FRACTION B: | |
| Water | 69.100 |
| Elestab ® 4121 (Serobiologic Laboratories) | 0.400 |
| *Terminalia Catappa* extract (obtained according to the process of Example I, diluted to 20% with propylene glycol) | 4.000 |
| Sodium cetostearyl sulfate | 1.200 |

The process of production of the above emulsion consists in separately preparing fractions A and B at 80° C., then introducing fraction A into fraction B at 80° C. under turbine agitation, then cooling the mixture obtained to 50° C. whilst maintaining turbine agitation, and, finally, cooling to ambient temperature whilst carrying out planetary agitation from 50° C.

Example 5

A cosmetic product in the form of an astringent protective gel eyeliner, according to the invention, can for example have a weight composition as indicated hereafter (association of fractions A, B and C):

| FRACTION A: | |
|---|---|
| Water | 70.925 |
| LS 48 stabilizer (Serobiologic Laboratories) | 0.225 |
| *Terminalia Catappa* extract (obtained by the process of Example I) | 0.100 |
| FRACTION B: | |
| Water | 24.175 |
| LS 48 stabilizer (Serobiologic Laboratories) | 0.075 |
| Carbomer | 0.750 |
| FRACTION C: | |
| Sodium hydroxide (N) | 3.750 |

The process for preparation of the above gel consists in preparing in the first instance, separately the fractions A and B, and then forming the gel in the second instance.

The preparation of fraction A consists in dissolving the LS 48 stabilizer in distilled water at 50° C., then dispersing in it the *Terminalia catappa* extract with turbine agitation and cooling the resulting mixture under planetary agitation to ambient temperature.

The preparation of fraction B consists in dissolving the LS 48 stabilizer in distilled water at 50° C., then dispersing it in the Carbomer with turbine agitation and cooling the resultant mixture with planetary agitation to ambient temperature.

To obtain the final gel, there is introduced at ambient temperature and with turbine agitation, the phases B and C into the phase A and then the mixture is homogenized by planetary agitation.

Example 6

A cosmetic product in the form of a soothing after-sun lotion, according to the invention, can for example have a weight composition as indicated hereafter (association of fractions A, B and C):

| FRACTION A: | |
|---|---|
| Dodecyl alcohol sulfate 39 C (alcohol phthalate) | 3.000 |
| Nonoxynol-14 | 0.600 |
| Perfume | 0.100 |
| FRACTION B: | |
| Propylene glycol | 2.000 |
| LS 48 stabilizer (Serobiologic Laboratories) | 0.300 |
| Water | 84.260 |
| Triethanolamine 20% aqueous solution | 0.240 |
| FRACTION C: | |
| *Terminalia Catappa* extract (obtained according to Example IV, diluted to 10% in propylene glycol) | 9.500 |

The process for preparation of the above lotion consists in separately preparing fractions A and C at ambient temperature and with agitation, preparing fraction B at 50° under agitation and cooling it to ambient temperature, introducing fraction A, then fraction C, into fraction B, letting the obtained mixture stand for 72 hours and finally filtering this latter.

Of course, the invention is not limited to the described embodiments. Modifications remain possible, particularly as to the constitution of the various elements or by substitution of technical equivalents, without thereby departing from the scope of protection of the invention.

What is claimed is:

1. Method for producing anti-inflammatory, soothing, astringent, firming or anti-stress repairing properties to the skin or external growths, comprising applying to the skin or external growths of a person in need of the same an effective quantity of dried extract of crushed leaves of the terminalia catappa plant, obtained by thermal extraction and by reflux with solvents selected from the group consisting of water, aqueous solutions of alcohols, ketones, halogenated hydrocarbons, esters, polyols and mixtures thereof all of by a separation from the solvent and drying thereof said amount to being effective to produce said anti-inflammatory, soothing astringent, firming or stress-repairing properties.

2. A method as claimed is claim 1, wherein said extract is applied in a composition containing between 0.005% and 20% by weight of said extract.

3. A method as claimed in claim 1, wherein said extract is applied in a composition containing between 0.10% and 3% by weight of said extract.

* * * * *